United States Patent [19]

Fujie

[11] Patent Number: 5,498,412
[45] Date of Patent: Mar. 12, 1996

[54] ANTIOXIDANT COMPOSITION AND METHOD FOR THE SAME

[75] Inventor: Hisanao Fujie, Kobe, Japan

[73] Assignee: A.O.A. Japan Co., Ltd., Hyogo, Japan

[21] Appl. No.: 322,013

[22] Filed: Oct. 11, 1994

Related U.S. Application Data

[63] Continuation-in-part of Ser. No. 164,551, Dec. 10, 1993, abandoned.

[51] Int. Cl.$^6$ .................................................. A61K 35/78
[52] U.S. Cl. .................................................. 424/195.1
[58] Field of Search .................................. 424/195.1

[56] References Cited

U.S. PATENT DOCUMENTS

| | | | |
|---|---|---|---|
| 5,009,891 | 4/1991 | Niwa et al. | 424/195.1 |
| 5,077,069 | 12/1991 | Chang et al. | 426/330.6 |
| 5,175,012 | 12/1992 | Shin et al. | 426/542 |

OTHER PUBLICATIONS

Minamiyama, Y. et al., "Antioxidant Effects of Natural Products (Antioxidant Biofactor; AOB)", The 5th International Congress on Oxygen Radicals: Active Oxygen, Lipid Peroxides and Antioxidants, (Nov. 17–21, 1991).
Komuro, E. et al., "Inhibition of Lipid Peroxidations by Antioxdant Biofactor", *Vitamins* 67 (9), 455–518 (1993).
Minamiyama, Y. et al., "Antioxidative Effects of a Processed Grain Food; Antioxidant Biofactor (AOB)", 1st World Congress of Dairy Products in Human Health & Nutrition (Jun. 7–10, 1993).
Minamiyama, Y. et al., "Protection by Antioxidant Biofactor (AOB), A Processed Grain Food, of Ischemia–Reperfusion Injury in the Rat Kidney", 1st World Congress of Dairy Products in Human Health and Nutrition (Jun. 7–10, 1993).
Hirai, et al., "Preventive and Antidotal Effects of Antioxidant Biofactor (AOB) on Paraquat–induced Acute Poisoning", 9th Annual Meeting of Japanese Society of Toxicologic Pathology, (1993).
Yoshikawa, T. et al., "Antioxidative Effects of Antioxidant Biofactor; AOB, a Processed Grain Food", Kyoto Prefectural University of Medicine (1992).
Minamiyama, Y. et al., "Free Radical Scavenging Effects of Natural Products (Antioxidant Biofactor; AOB)", 3rd International Symposium on Spin Trapping & Aminoxyl Radical Chemistry, Nov. 22–24, 1991.
Minamiyama, T. et al., "Antioxidant Effects of Natural Products (Antioxidant Biofactor; AOB)", 5th International Congress on Oxygen Radicals (Nov. 17–21, 1991).
Minamiyama, Y., et al., "Superoxide Scavenging Activity and Antioxidative Effect of Antioxidant Biofactor (AOB)", The 15th Japanese Society of Lipid Peroxide and Free Radical Research, (Nov. 1991).
Minamiyama, Y. et al., "A Study of Antioxidant Biofactor (AOB), a Processed Grain Food, on Superoxide Scavenging Activity by ESR Spin Trapping Method", The 8th General Meeting of Medical and Pharmaceutical Society for Wakan–Yaku, (Aug. 1991).
Hirai et al., "Restraint Effect of AOB Against Paraquat Toxicity in Mice (Preliminary Experimentation)", Kanazawa Medical University (1992).
Tanizawa et al., Chem. Pharm. Bull., 32(5), pp. 2011–2014, (1984).
Wang et al., Chung Hsi I Chieh Ito Tsa Chih, 11(3), pp. 159–161 (1991–Mar.).

*Primary Examiner*—John W. Rollins
*Attorney, Agent, or Firm*—Foley & Lardner

[57] ABSTRACT

A natural antioxidant composition made from a plurality of fermented and milled materials of edible grains and pulses and an embryo or bran of the grains, is produced by a process comprising the steps of: parching a plurality of kinds of edible grains and pulses and an embryo or bran of the grains and pulses respectively; milling the parched resultants separately; steaming the milled resultants separately; molting the steamed resultants separately with fermentations; adding alcohol to the malted resultants separately to restrict the fermentations; drying the resultants separately to remove the alcohol; mixing all of the resultants to make a first mixture fermented; parching an edible seed and a green tea leave separately; milling the parched seed and the parched green tea leave separately; mixing the parched seed and the parched green tea leave to make a second mixture of mash; mixing the first and second mixtures to a mature material; and granulating the mature material to granules, thereby being easily digested in the aged human body without pyrosis or heartburn.

5 Claims, 4 Drawing Sheets

5,498,412

ANTIOXIDANT COMPOSITION AND METHOD FOR THE SAME

CROSS REFERENCE TO RELATED APPLICATION

This is a continuation-in-part of U.S. application Ser. No. 164,551, filed Dec. 10, 1993, now abandoned.

BACKGROUND OF THE INVENTION

1. Field of the Invention

The present invention relates to a natural antioxidant composition, more particularly to a natural antioxidant composition of a processed grain food used for maintaining human health and preventing from diseases so to assist a medical treatment.

2. Description of the Related Art

It is believed in the field of medicine and biochemistry that one of the causes of maturity-onset diseases such as arteriosclerosis, cancer, cardiopathy, diabetes mellitus is due to active oxygens or its free radicals (hereinafter referred as "active oxygen") generated in the tissues or cells of a living body. The relationship between the disease and the active oxygen has been studied.

The active oxygen causes merits and demerits in the living tissue. Namely, the active oxygen at a adequate amount performs a part of the defensive mechanism against an infection. On the other hand, when the active oxygen excessively generated in the tissue, such surplus active oxygen causes a reaction of lipid peroxidation by means of non-control denatures nucleic acids and proteins. As a result, the surplus active oxygen becomes the causes of diseases of adult people and incurable diseases. This surplus active oxygen is a great problem as unnecessary oxidation in the living tissue. For this, the inhibiting enzymes effectively preventing such a so-call toxicity of active oxygen are generated in the living tissue. Superoxide dismutase (hereinafter referred as "SOD") is well known as one of the inhibiting enzymes. There is a treatment method for curing the disease by injecting SOD into the living tissue. SOD is administered only by means of the subcutaneous injection. The duration of effect of SOD is only for about ten minutes. The effect of SOD is not confirmed, when SOD is used in the form of an oral medicine. The advantageous effect of SOD is restricted, so that it is effective against only the disease caused by lacks of SOD. There are six kinds of active oxygens concerning the reaction of lipid peroxidation and the other four kinds.

Japanese patent application publication No. 61-29711 discloses a method for making a nutrient food comprising the steps of: mixing a parched and milled rice flour with bran, yellow flour and green tea flour; adding *Aspergillus oryzae* or Koji thereto to make a powdered mixture material; and dipping the powdered material to the mixed vegetable oil comprising sesame oil and soybean oil for four days to extract effective contents with the mixed oil. Although this nutrient food against the active oxygen has SOD-like effect, but its effect is insufficient. It is therefore desired to develop a composition having a high antioxidant activity in the living tissue by an oral administration thereof.

U.S. Pat. No. 5,009,891 discloses an antioxidant composition of natural products for scavenging the active oxygen which is manufactured through the steps of: heating a plant seed, grains and germs; adding a microorganism; brewing or fermenting the mixture; and adding a vegetable oil extracted from heated plants. This publication also discloses another antioxidant composition produced by adding vitamin C or derivatives thereof to the forgoing composition.

The natural antioxidant composition has an activity for counteracting the active oxygens excessively generated in the living tissue. It is believed that, when the active oxygens are excessively generated the defensive mechanism against an infection in the living tissue, the surplus active oxygens cause cerebrovascular disease, circulation disease, eye disease, diabetes mellitus or cancer, and influence an age-related disease, inflammation or the like. However, the natural antioxidant composition is effective against diseases of adult people and incurable diseases such as malignant dysarthrosis rheumatism, Behçet's disease, Crohn disease, ulcer colitis and so on and, in addition, it preferably used for treats or preventions of a burn, an external wound, a fatigue, a hangover and a constipation to effect the maintenance of human health.

However, there is a problem that the conventional antioxidant composition contains the vegetable oil which is easily oxidized, so that the oxidized oil promotes to increase lipoperoxides with active oxygens to be suppressed in the living boy. The conventional antioxidant composition containing the vegetable oil restricts its activity for scavenging active oxygens and preventing the lipid peroxidation, itself.

Further, there is another problem that the conventional antioxidant composition is not easily digested to lie heavy on the stomach and brings pyrosis or heartburn according to the circumstances when people with a small secretion of the salivary and/or gastric juice such as the aged eat it, because of the added vegetable oil in the antioxidant composition.

SUMMARY OF THE INVENTION

In view of the forgoing status, the present invention has been made to solve such a problem. An object of the invention is therefore to provide a composition having a high antioxidant activity in the living tissue and being easily digested in the aged human body without pyrosis or heartburn.

The present invention provides a natural antioxidant composition made from a plurality of fermented and milled materials of edible grains and pulses and an embryo or bran of the grains, which is produced by a process comprising the steps of:

parching a plurality of kinds of edible grains and pulses and an embryo or bran of the grains and pulses respectively;

milling the parched resultants separately;

steaming the milled resultants separately;

malting the steamed resultants separately with fermentations;

adding alcohol to the malted resultants separately to restrict the fermentations;

drying the resultants separately to remove the alcohol;

mixing all of the resultants to make a first mixture fermented;

parching an edible seed and a green tea leave separately;

milling the parched seed and the parched green tea leave separately;

mixing the parched seed and the parched green tea leave to make a second mixture of mash;

mixing said first and second mixtures to a mature material; and granulating the mature material to granules.

The inventor has revealed that the obtained natural product has a high living-tissue-antioxidant activity for scavenging selectively surplus active oxygens and preventing the reaction of lipid peroxidation and being easily digested in the aged human body without pyrosis or heartburn.

In this natural antioxidant composition for the living tissue according to the present invention, it is preferable to use at least two edible grains and pulses selected from a group comprising rice, wheat, soybean, maize, adlay, red beans or the like, preferably soybean, adlay. Embryos of various edible grains and pulses above-mentioned are used and, wheat embryo, and rice bran are used preferably.

A preferable combination of edible grains and pulses is a set of soybean, adlay, wheat embryo and rice bran at an using ratio of 2:1:1:2=soybean: adlay: wheat embryo: rice bran. High quality and fresh materials are preferably used. In embryos, rice bran immediately after polished is preferably used since rice bran is easily oxidized.

In the parching step of the present invention, "parching" means to heat materials such as edible grains and pulses under conditions that heat is sufficient to decompose polymerized effective contents into small molecular components without the materials being scorched.

The parching temperatures are adjusted according to kinds of edible grains and pulses and heating periods respectively. Generally, the parching is sufficiently performed at a temperature of 80–90 centigrade for 5–6 hours. The heating means should be employed which is capable of homogeneous heating so as to minimize the difference of temperatures between the inside and outside layers of each particle of grains and pulses or embryos. In the purpose of this heating, a method using irradiation of a far-infrared ray may be used. A method for depositing the object in an isothermal bath or a moving floor is also employed in order to homogeneously heat them. A kiln or container made of stone or ceramic is preferably used.

After the edible grains and pulses materials are parched respectively, the parched materials are separately powdered in the milling step every kind of grains and pulses. In case it is not necessary to strictly and finely powder the materials, because Koji or *Aspergillus oryzae* is merely mixed with the material in the hereinafter molting step.

After the milling step, the parched and powdered materials are steamed respectively in the steaming step. To steam the material is performed through a conventional method in such a manner that the materials are excessively steamed respectively. This steaming step facilitates to next ferment the materials. An excessive steaming promotes the excess fermentation of each material. This steaming is performed to provide a certain dampness for the powdered material.

After the steaming step, Koji or *Aspergillus oryzae* for the fermentation is inoculated to the steamed powdered material. The fermentation includes the decomposition of organic materials by microorganism and the reaction that the metabolic substance becomes simple compounds. For example, it is preferable that the fermentation is gradually performed by *Aspergillus oryzae* or yeast or the like. In the fermenting step, since Koji or *Aspergillus oryzae* contains enzymes such as amylase, protease of the like, the activity of the enzymes promotes that proteins becomes small molecular substances so that the small molecular substances easily saturate into the living tissue to enhance the antioxidant activity.

In the malting step, the steamed materials are inoculated per each kind of materials. Three kinds or more of powdered yeasts are previously prepared so that the suitable yeasts for the materials are prepared by mixing the different yeasts. It is preferable that the powdered yeasts are sufficiently mixed to the corresponding steamed materials respectively. After the inoculation of the powdered materials, these materials are transferred to containers made of ceramic or plastic respectively, and then the fermentations are performed at the aging temperature of 35–36 centigrade for at least three days through two weeks. The adjusting of temperature in the materials should be sufficiently noted because of fluctuation of the atmospheric temperature and humidity. Antioxidant substances are produced during the aging step.

After the malting step, alcohols are added to the fermenting malt materials respectively to stop the fermentations thereof, while the materials are stirred.

The malted materials are dried in the drying step to remove alcohols respectively, so that the fermentations are terminated respectively. The drying is performed by means of a conventional dryer at the dry temperature of 100 centigrade or less.

After the drying of materials, these malt materials are milled respectively, preferably at about 400 mesh of Tyler Standard screen scale by a conventional milling method. These all milled materials are mixed. The milling method is not restricted. The finely powdered materials improve the saturation and digestion of components thereof in the living tissue. In this way, a first mixture of the fermented and milled material is obtained.

On the other hand, the following materials are prepared separately from the forgoing first mixture. Namely, edible seeds are parched and mashed to make a dry mash. Vegetables containing vitamin C or vitamin C derivatives (hereinafter referred as "vitamin C-vegetables") are dried and milled to make another wet or dry mash. These two mashes are mixed and stirred so that a second mixture is produced.

The used edible seeds are selected from a group comprising sesame, soybean, maize, rape-seed and so on. The most preferable seed is sesame, because sesame contains lots of vitamin E inhibiting the lipid peroxidation. These edible seeds should be used after parched in the parching step.

The used vitamin C-vegetables are selected from a group comprising tea leaves, young leaves of radishes, lemon or Yuzu orange or citron, and spinach or the like, but not restricted by these plants. Lemon, Yuzu orange, citron or the like or the mixture thereof is used in the from of a fruit juice squeezed. The green tea leaves are preferably used. It therefore preferable that the combination of tea leaves, young leaves of radishes and a juice of Yuzu or citron is employed for the second mixture. These components prevent oxidation of edible seeds. These vitamin C-vegetables are preferably dried and milled excepting fruits. Particularly, tea leaves is parched and dried by a conventional heating method to powdered up to a particle size of 500 mesh of Tyler Standard screen scale, preferably.

The using ratios of the edible seed mash and the vitamin C-vegetables are, for example, the tea-vegetables of 10 parts by weight and the edible seed of 5 parts by weight with respect to the first mixture of the fermented and milled material 85 parts by weight, alternatively, the tea-vegetables of 5 parts by weight and the edible seed of 5 parts by weight with respect to the fermented material of 90 parts by weight.

Next, the forgoing second material mixture of tea leaves, sesame, young leaves of radishes and a juice of Yuzu or citron is added to the first mixture of the fermented and milled materials while sufficiently stirred. After this mixing step, this final mixture is a mature material flour.

This mature material flour contains the moisture of about 12%. Since this moist material probably ferments again, it is dried and granulated in the granulating step to improve the mobility of the flour. This granulation of the mature material flour is performed by means of a material granulating dryer in which the flour is granulated and dried in a vacuum chamber. In this way, natural antioxidant composition is accomplished for the first time.

DESCRIPTION OF THE PREFERRED EMBODIMENT

An preferred embodiment according to the present invention will be described below in detail with reference to the accompanying drawing, but the present invention is not restricted by the following embodiment.
(Preparation of natural antioxidant composition)

Figure 1:
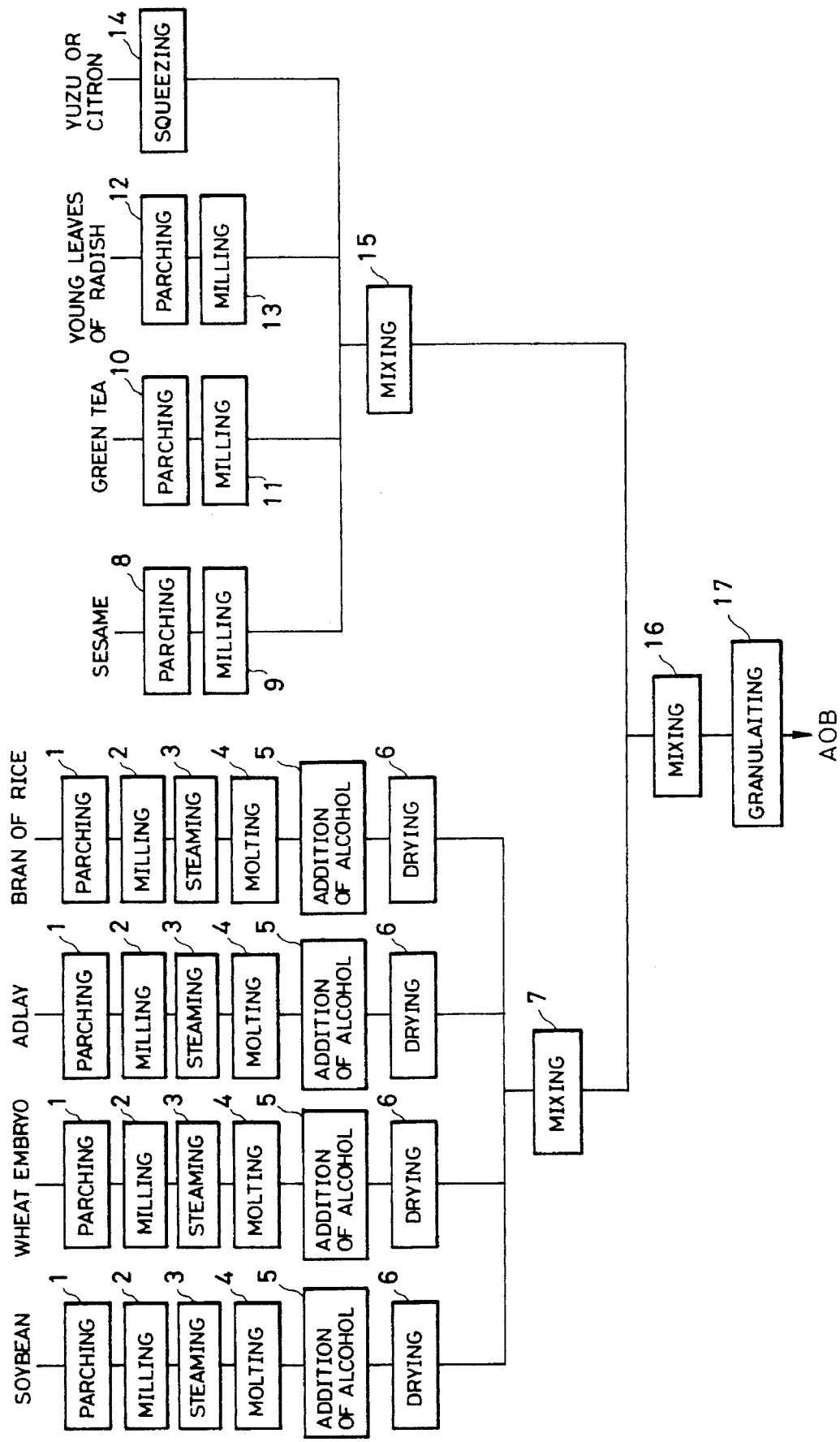
FIG. 1 is a schematic diagram showing a flow-chart of the method for producing a natural antioxidant composition according to the present invention.

A flesh row materials of soybean 30 parts by weight, a wheat embryo 15 parts by weight, an adlay 15 parts by weight and a bran of rice immediately after polished 30 parts by weight were parched separately, as shown in the step 1 of FIG. 1. Soybean, wheat embryo, adlay and bran were homogeneously heated and parched in a corresponding individual isothermal baths at temperature 80 centigrade for 5 hours, respectively. After that, these material seeds were milled to be powdered materials, as shown in the step 2 of FIG. 1.

The parched powders were steamed at a temperature of 110–120 centigrade for 30 minutes respectively, as shown in the step 3 of FIG. 1.

Next, *Aspergillus oryzae* were added to the steamed and powdered materials to be sufficiently mixed and inoculated respectively. The inoculated powders were transferred to different ceramic containers to be maintained at a temperature of 35–36 centigrade for 2 weeks respectively to be fermented as a molting step 4 of FIG. 1.

After malting sufficiently, alcohols were added to malted materials respectively and the materials were stirred to stop the fermentations, as shown in the step 5 of FIG. 1.

After the addition of alcohols, the materials were dried at temperature 100 centigrade as shown in the step 6 of FIG. 1. The dried malt materials were milled to 400 mesh of Tyler Standard screen scale to be fine grains respectively.

All of the obtained powdered materials were mixed to be a fermented material as the first mixture, as shown in the step 7 of FIG. 1.

Separately from the above steps preparing the fermented material, sesame was parched and mashed, as shown in the steps 8 and 9 of FIG. 1.

In addition, green tea leaves were parched while stirred and then mashed, as shown in the steps 10 and 11 of FIG. 1, so that a dried tea leaves powder of 500 mesh of Tyler Standard screen scale was prepared.

Whereas young leaves of radishes were parched while stirred and then mashed, as shown in the steps 12 and 13 of FIG. 1, so that a dried leaves powder of 500 mesh of Tyler Standard screen scale was prepared.

Yuzu or citrons were squeezed to extract juices thereof, as shown in the step 14 of FIG. 1.

These sesame mash, green tea leaves powder, young leaves of radishes and a juice of Yuzu or citron are mixed while sufficiently stirred so that the second mixed material is obtained, as shown in the step 15 of FIG. 1.

This second mixed material was added to the fermented material (the first mixture) previously prepared and sufficiently stirred so that the mature material flour was obtained, as shown in the step 16 of FIG. 1. The using ratios was the green tea or the like of 10 parts by weight and the edible seed powders 5 parts by weight with respect to the fermented first mixture of 85 parts by weight. For the using ratios, the green tea or the like of 5 parts by weight and the edible seed leaves powders 5 parts by weight with respect to the fermented material of 90 parts by weight may be accepted.

Next, the material flour was granulated to granules of a natural antioxidant composition by means of a granulator, as shown in the step 17 of FIG. 1. In this way, natural antioxidant composition or Antioxidant biofactor (hereinafter referred as "AOB") is produced.

The lipid peroxidation scavenging effect of AOB through the above-mentioned process, was confirmed by the following animal experiment.
(Experiment and method)

All animals used for the Experiments were male SD rats (Sprague-Dawley rat)(Body Weight: 200 grams–220 grams).

In vitro experiment, AOB was prepared for 0.5% CMC suspension. TBA (Thiobarbituric Acid) reactive substances were measured on the lipid peroxidation in rat brain homogenate.

Ex vivo experiment, each rat was kept in separated cage for an AOB group and a control group. The rats of the control group were fed the basal diet. The rats of the AOB group were fed the mixture of the basal diet and 1 grams or 5 grams of AOB. Rats of both groups were fed for one or three days. After that, blood plasma was extracted from each rats. The plasma was used for samples of the ESR method. The study of ESR (Electron Spin Resonance) was performed by using a spin trapping agent such as DMPO (5,5-dimethyl-1-pyrroline-1-oxide) and the ESR spectrometer (JEOL-JES-FR80: JEOL, Co., Ltd.,). We studied the superoxide scavenging activity in the AOB suspension and blood plasma by using the superoxide generating system (hypoxanthine-xanthine oxidase).

As a result, in the ESR spin trapping method, the blood plasma of the AOB group had a superoxide scavenging activity in vitro and ex vivo experiments. Superoxide 50% inhibition $IC_{50}$ in the AOB suspension was 42 µg/ml. The blood plasma solution of the control group diluted 12 times showed 0.152 plus or minus 0.017 U/ml (converting into SOD activity). The blood plasma samples of AOB group (1 g/day/rat) after fed for 1 and 3 days showed 0.233 plus or minus 0.01 U/ml and 0.280 plus or minus 0.042 U/ml respectively. The blood plasma samples of AOB (5 g/day/rat) after fed for 1 and 3 days showed 0.233 plus or minus 0.016 U/ml or 0.280 plus or minus 0.042 U/ml. AOB further strongly inhibited the lipid peroxidation in rat brain homogenate. $IC_{50}$ was 8 µg/ml.

Accordingly, it is understood the AOB containing flavonoid, tannin, tocophenols, ascorbate and so on has a very strong antioxidant activity. It may be presumed that this strong antioxidant activity of AOB appears as a result of overall additive and synergistic effects of the contents thereof and non-addition of the vegetable oil being easily oxidized to increase lipoperoxides.

Inventor confirmed that AOB of antioxidant composition was easily digested without pyrosis or heartburn even when the aged people with a small secretion of the salivary and/or gastric juice eat it, because no addition of the vegetable oil in the antioxidant composition.

According to the present invention, a plurality of kinds of edible grains and pulses and/or embryos or bran are parched respectively, after that, each milled, steamed, malted, and terminated those fermentations by the adding of alcohol and the products dried in sequence so that all of the powdered materials are mixed, and then the mixed fermented material is mixed with edible seeds and vegetables containing vitamin C or vitamin C derivatives to be stirred to be granulated to a natural antioxidant composition. This composition and is capable of effectively inhibiting surplus active oxygens excessively generated in a living tissue and being easily digested in the aged human body without pyrosis or heartburn.

Inventor has studied another advantageous effect of AOB and paid attention to the effect the SOD-like activity above mentioned and presumed that there is the possibility of changing the life of nitric oxide (NO) in the living body. Namely, Nitric oxide is well-known as an endothelium derive relaxing factor (EDRF) and a potent vasorelaxant, but its half life is very short. Nitric oxide is decomposed by superoxide radicals, but protected by SOD.

Therefore, since AOB has SOD-like activity, it is possible that AOB can change the fate of NO when the NO donor such as nitroglycerine, NOC7 etc. is injected to the living body e.g. rats.

The effect of AOB on the fate of NO in the living body was tested by the detection of NO-Hb (nitric oxide—haemoglobin) as follows:

NOC7 (Dojin) represented by the following formula was used for the NO donor releasing NO spontaneously without a co-factor.

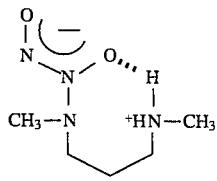

Male Wister rats (BW; 300 g) were kept in separated cages for an AOB group and a control group. The rats of the control group were fed only the basal diet. The rats of the AOB group were fed the mixture of the basal diet an AOB which was treated 3 g/rat/day for 3 days.

The changes of blood pressure level and NO-Hb level were measured at 10, 30, 60, 120 and 180 minutes after NOC7 was injected 10 μmol/kg,iv. into each rat. The concentration of NOx was measured at 240 minutes after NOC7 was injected 10 μmol/kg,iv. into each rat.

Figure 2:
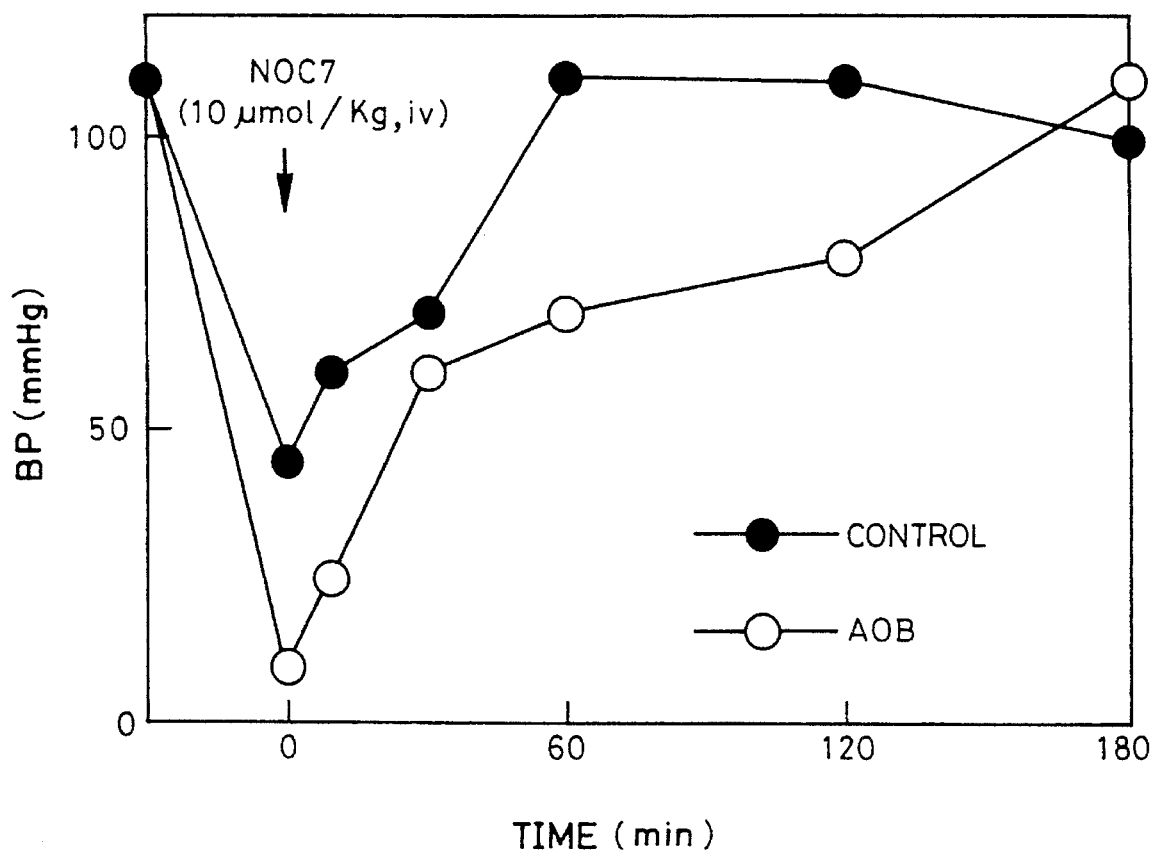
FIG. 2 is a graph showing depressing effects of blood pressure (BP) caused by NOC7 and AOB+NOC7 in the rats.
Figure 3:
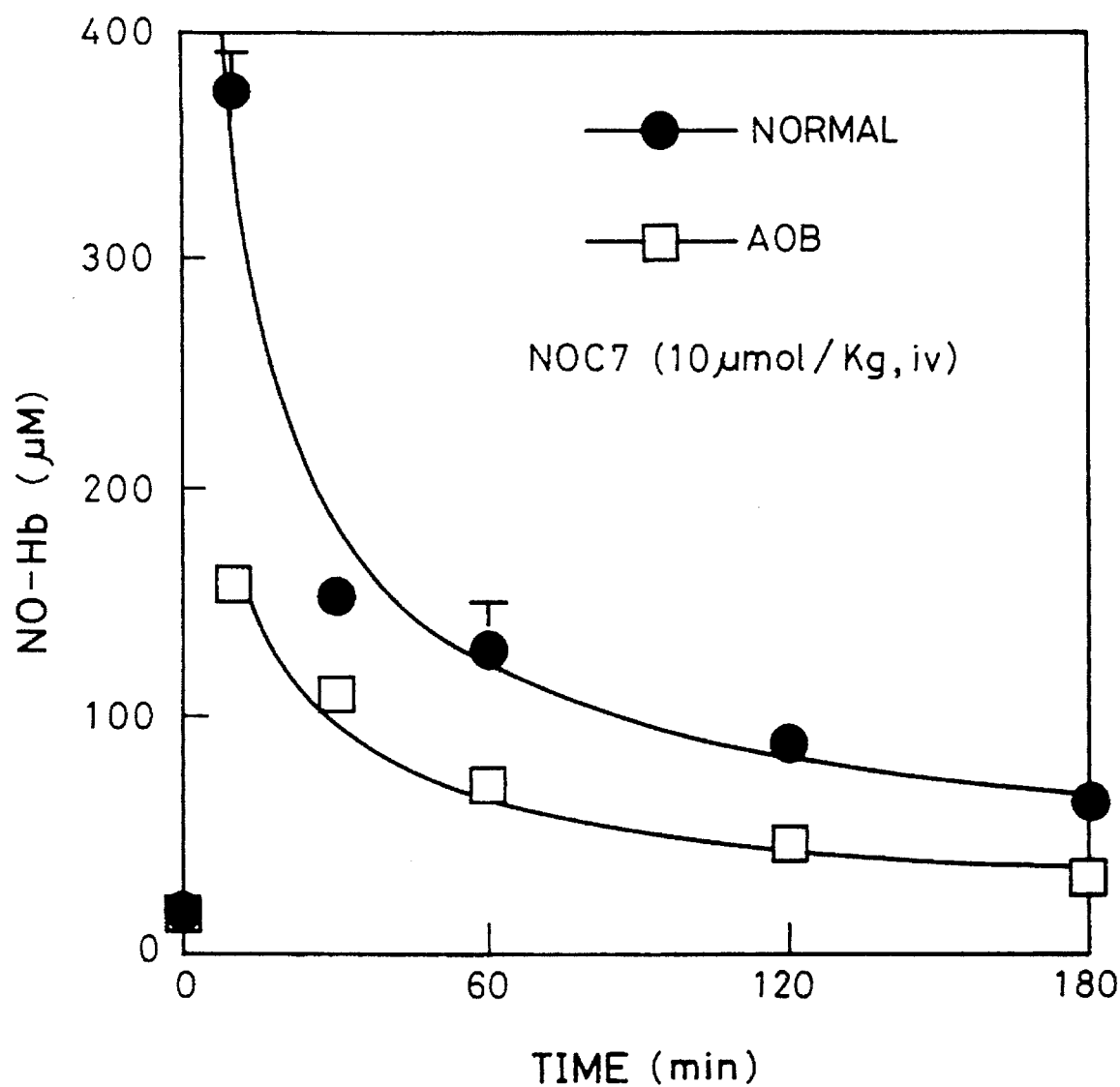
FIG. 3 is a graph showing levels of NO-Hb produced by NOC7 in the rats.
Figure 4:
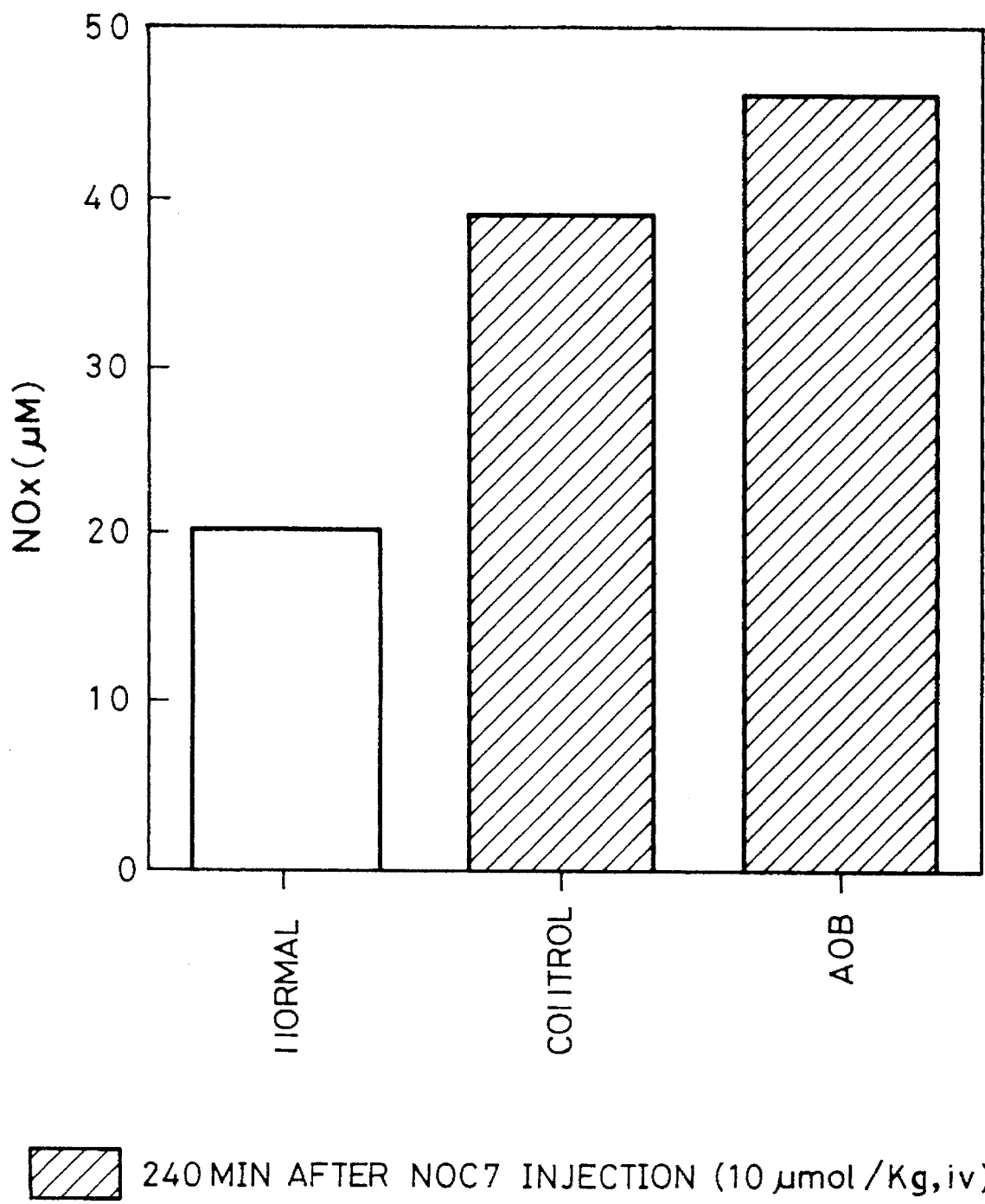
FIG. 4 is a graph showing the concentration of NOx measured at 240 minutes after NOC7 injection in the rats.

As a result, effects of depression effect of blood pressure (BP) due to NOC7 are shown in FIG. 2 in which black plots indicates BP of the control group and white plots indicates BP of the AOB group. FIG. 3 is a graph showing levels of NO-Hb produced by NOC7 in the circulation of the rat in which black plots indicates NO-Hb of the control group and white plots indicates NO-Hb of the AOB group. FIG. 4 shows the concentration of NOx measured at 240 minutes after NOC7 injection.

It is understood in FIG. 2 that the treatment of AOB potentiates the relaxant activity of NOC7 producing nitric oxide. It is confirmed in FIG. 3 that the formation of NO-Hb in the control group was grater than that in the AOB group. It is understood in FIG. 4 that there is little difference in the NOx level between both groups. Since the NOx level of the AOB treated rat is not significantly different from that of the control rat, AOB does not act on the generation of NO from NOC7.

These results suggest a chemical interaction between AOB or its metabolites and nitric oxide, leading to the formation of a novel potent vasodilator.

Accordingly, the administration of AOB for a long time is more useful for remaining nitric oxide in endothelium to normalize the blood pressure.

What is claimed is:

1. A method for producing a natural antioxidant composition made from a plurality of fermented and milled materials of edible grains and pulses and embryos or brans thereof, comprising the steps of:

separately parching a plurality of members selected from the group consisting of at least one edible grain, at least one edible pulse, at least one embryo of an edible grain, at least one embryo of an edible pulse, at least one bran of an edible grain and at least one bran of an edible pulse at a temperature between 80 and 90 degrees centigrade for between 5 and 6 hours;

milling each of the parched resultants separately;

steaming each of the milled resultants separately;

malting each of the steamed resultants separately with fermentation at an aging temperature between 35 and 36 degrees centigrade for between 3 and 14 days;

adding alcohol to each of the malted resultants separately to restrict the fermentation;

drying each of the resultants separately to remove the alcohol at a drying temperature of 100 degrees centigrade or less and separately milling each at about 400 mesh of Tyler Standard screen scale;

mixing all of the resultants to make a fermented mixture;

separately parching an edible seed, green tea leaves and at least one member selected from the group consisting of young leaves of radish and spinach;

milling each of the parched seed, the parched green tea leaves and the parched radish and/or spinach leaves separately;

squeezing at least one member selected from the group consisting of lemon, Yuzu orange and citron, and recovering a juice;

mixing the milled parched seed, the parched green tea leaves, and the radish and/or spinach leaves and the juice to make a mash;

mixing said fermented mixture and said mash to form a complete material; and granulating the complete material to granules.

2. A method for producing a natural antioxidant composition according to claim 1, wherein said edible grains and pulses comprise at least two grains or pulses selected from the group consisting of soybean, adlay, wheat and rice; said embryos and brans comprise at least one embryo or bran selected from the group consisting of rice and wheat; and said edible seed is sesame.

3. A method according to claim 1, wherein said plurality of said edible grains and pulses comprises soybean, adlay, wheat embryo and rice bran in a ratio of 2:1:1:2, respectively.

4. A method according to claim 1, wherein said complete mixture comprises 10 parts by weight of said milled young leaves and said squeezed juice, 5 parts by weight of said edible seed, and 85 parts by weight of said fermented mixture.

5. A method according to claim 1, wherein said complete mixture comprises 5 parts by weight of said milled young leaves and said squeezed juice, 5 parts by weight of said edible seed, and 90 parts by weight of said fermented mixture.

\* \* \* \* \*